United States Patent [19]

Jerge et al.

[11] Patent Number: 4,541,992
[45] Date of Patent: Sep. 17, 1985

[54] APPARATUS FOR ORGANIZING, STERILIZING, AND MAINTAINING MEDICAL/DENTAL INSTRUMENTS

[75] Inventors: Charles R. Jerge, Winston-Salem, N.C.; Bruce Frankel, Northbrook; Karl Zoll, Glenview, both of Ill.

[73] Assignee: Hu-Friedy Manufacturing Co., Chicago, Ill.

[21] Appl. No.: 522,451

[22] Filed: Aug. 10, 1983

[51] Int. Cl.⁴ ............................................. A61B 19/02
[52] U.S. Cl. .................................... 422/300; 422/310
[58] Field of Search ................ 422/299, 300, 302, 310

[56] References Cited

U.S. PATENT DOCUMENTS 4,135,868  1/1979  Schainholz ........................... 422/300
4,327,060  4/1982  Nisii .................................... 422/310

OTHER PUBLICATIONS

Svenska Dental Instruments AB, Vasby, Sweden, prior to 8/10/83.
Syntex Dental Products, Inc., Bay Minette, AL, 3/82, prior to 1/10/83.
A-dec Trays & Tubs, Newberg, OR, prior to 8/10/83.
Medin Corporation, Instrument Tray for Microsurgery, prior to 8/10/83.
Aesculap, Tuttlingen, West Germany, prior to 8/10/83.
Winston-Salem Dental Care Plan, Inc., Winston-Salem, North Carolina, prior to 8/10/83.

*Primary Examiner*—John Adee
*Attorney, Agent, or Firm*—Laff, Whitesel, Conte & Saret

[57] ABSTRACT

A sterilizable, stackable medical/dental instrument casette is formed of sterilization heat resistant plastic. A cover of the casette is closable, openable and separable from a tray of the casette. The tray is stackable on the cover, or other identical casette covers. Flexible, movable rails define compartments within the casette, and support and separate instruments in the casette. The cover is securely latchable to the tray.

11 Claims, 9 Drawing Figures

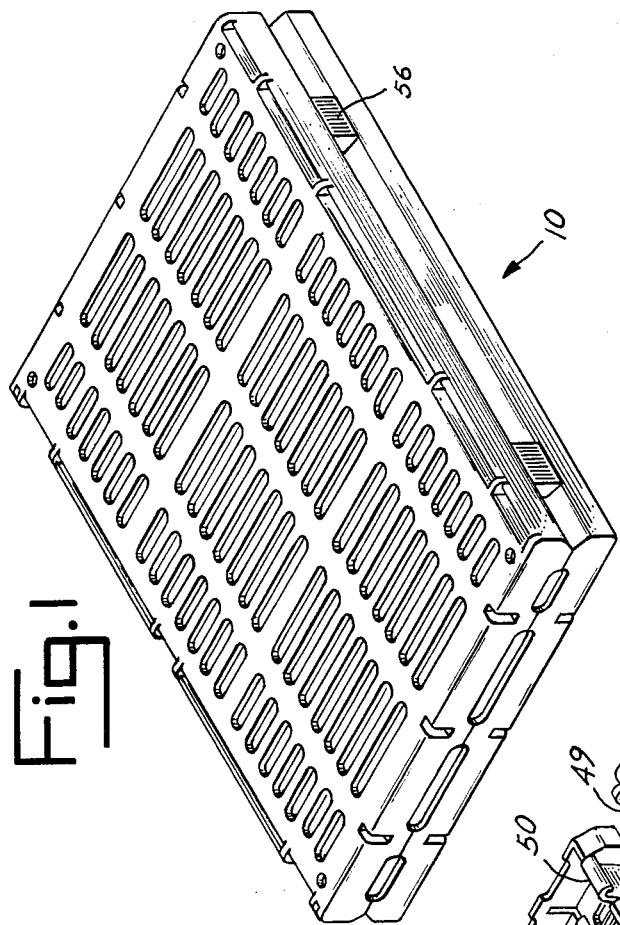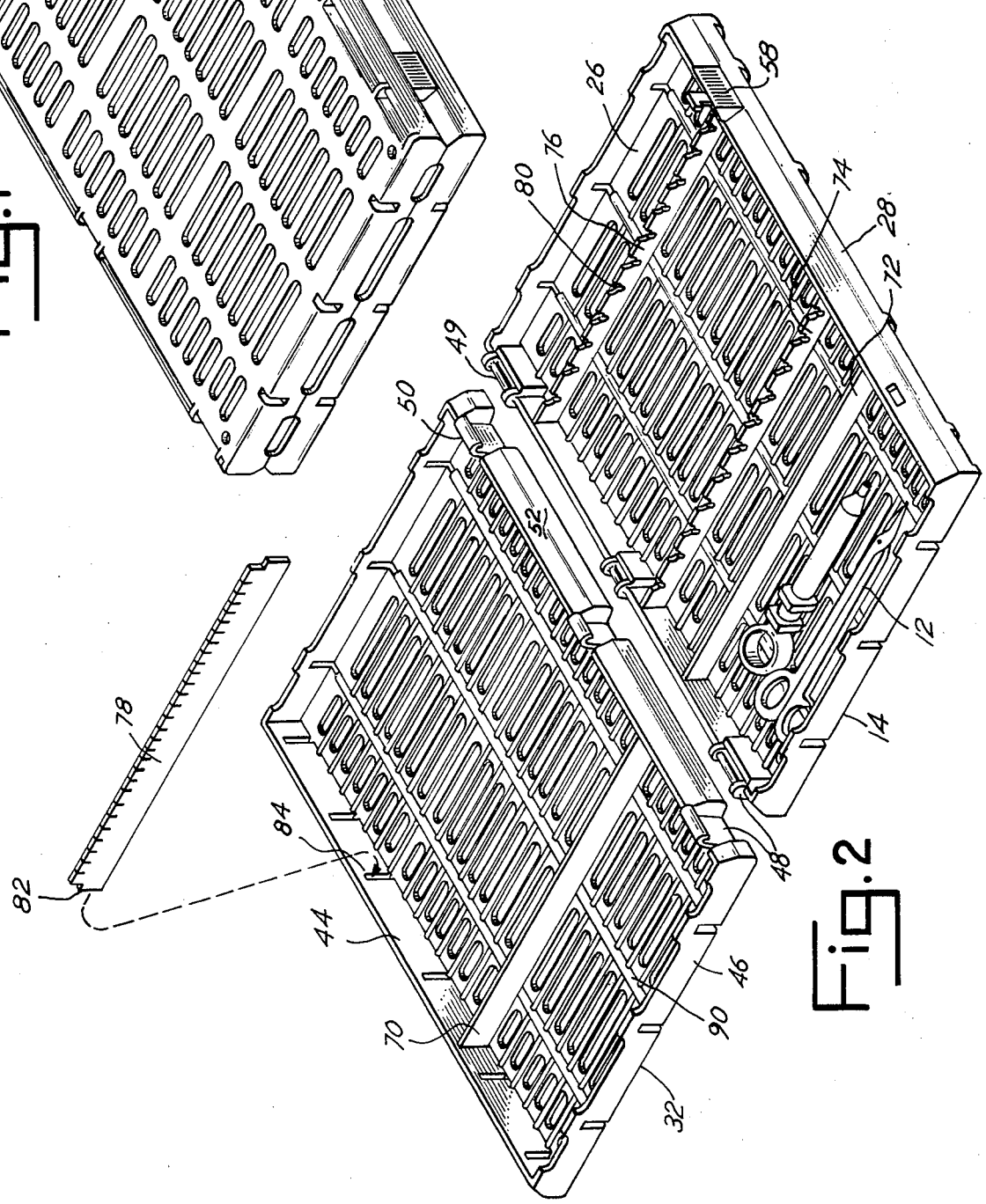

APPARATUS FOR ORGANIZING, STERILIZING, AND MAINTAINING MEDICAL/DENTAL INSTRUMENTS

BACKGROUND OF THE INVENTION

This invention relates to medical/dental instrument trays, and more particularly to a dental instrument casette.

In the past, dental instruments were sterilized while loose, and selected during operations from an array of instruments, by name. In the more recent past, dental instruments have been sterilized while loose, and organized before operations in trays, to be taken from the trays and used in the sequence in which placed in the trays. Most recently, dental instruments have been organized in trays first, and then sterilized and used. However, the trays most recently in use have been reinforced wire mesh baskets. They have been costly, unstackable, with hinged lips difficult to keep open, subject to rust, discoloration, breakage, and debris entrapment.

SUMMARY OF THE INVENTION

The object of the inventors in making this invention was to achieve a medical/dental instrument casette with the advantages of past trays, without the disadvantages. Another object was to provide a dental instrument casette which was rugged, versatile, safe to handle, inexpensive, stackable in number and over its own top, and pleasing of appearance.

Thus, in a principal aspect, the present invention is a sterilizable, stackable, medical/dental instrument casette. The casette comprises, first, a tray of sterilization heat resistant material having a plurality of sterilization openings, and a cover of sterilization heat resistant material having a plurality of sterilization openings. Hinge means is on the cover and the tray for releasably hingeably joining the cover to the tray. The cover and tray are thereby separable and hingedly movable to and from open and closed positions. Latch means of sterilization heat resistant material is on the cover and tray for releasably latching the cover to the tray in the closed position. Instrument retaining means of sterilization heat resistant material is also on the cover and tray for releasably retaining dental instruments within the closed cover and tray remote from contact, in at least a first fixed arrangement and in both the open and closed positions of the cover and tray. Finally, stacking means of sterilization heat resistant material is on the cover and tray for stacking the tray over the cover while separated therefrom.

Thus, the medical/dental instruments and casette may be repeatedly cycled through a process of placement of the instruments in the casette in the fixed arrangement, sterilization of the instruments and closed casette together, use of the sterilized instruments, and return of the instruments to the casette.

These and other aspects, objects and advantages of the invention are provided in a detailed description of the preferred embodiment of the invention, which follows a brief description of the drawing.

BRIEF DESCRIPTION OF THE DRAWING

The preferred embodiment of the invention is the casette shown in the accompanying drawing of three sheets and nine figures or FIGS. The figures are as follows:

FIG. 1 is a first perspective view of the preferred casette, closed;

FIG. 2 is a second perspective view of the preferred casette, open to reveal internal features and representative contents;

DETAILED DESCRIPTION OF THE PREFERRED EMBODIMENT

Referring to FIG. 1, the preferred embodiment of the invention is a sterilizable, stackable, medical/dental instrument casette 10. The casette 10 is useful for repeatedly cycling through a process of use and autoclave sterilization in which instruments such as instrument 12 (FIG. 2) are placed and kept in loose and fixed arrangements in the casette. The instruments are removed from the casette only for use, repair or replacement. The casette is adaptable to a plurality of pre-selected, fixed arrangements of instruments, as will be described.

Figure 6:
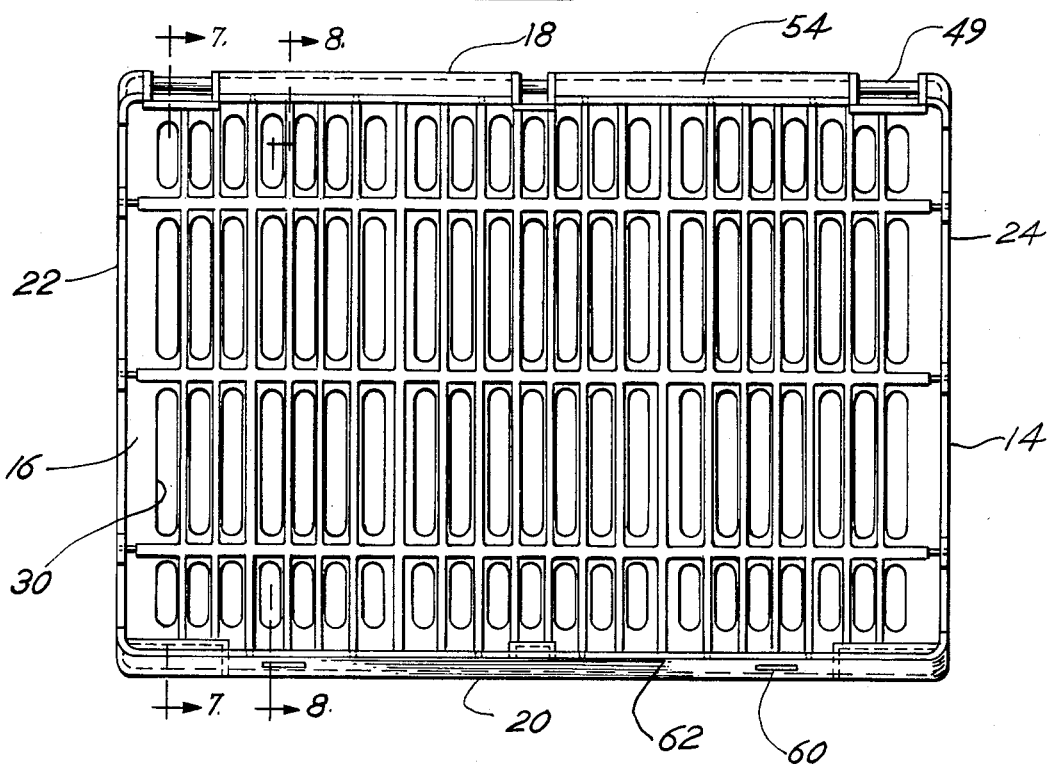
FIG. 6 is a plan view of the casette tray, from above.
Figure 7:
FIG. 7 is a first section view of the casette tray, taken from along line 7—7 of FIG. 6.

A rectangular tray 14 of the casette has a bottom 16 (FIG. 6) and four tray sidewalls 18, 20, 22, 24 defining a tray interior 26 and a tray exterior 28. The bottom and tray sidewalls are formed of sterilization heat resistant plastic, and are perforated substantially completely with a plurality of sterilization openings 30 from the tray exterior 28 (FIG. 2) to the tray interior 26.

Figure 3:
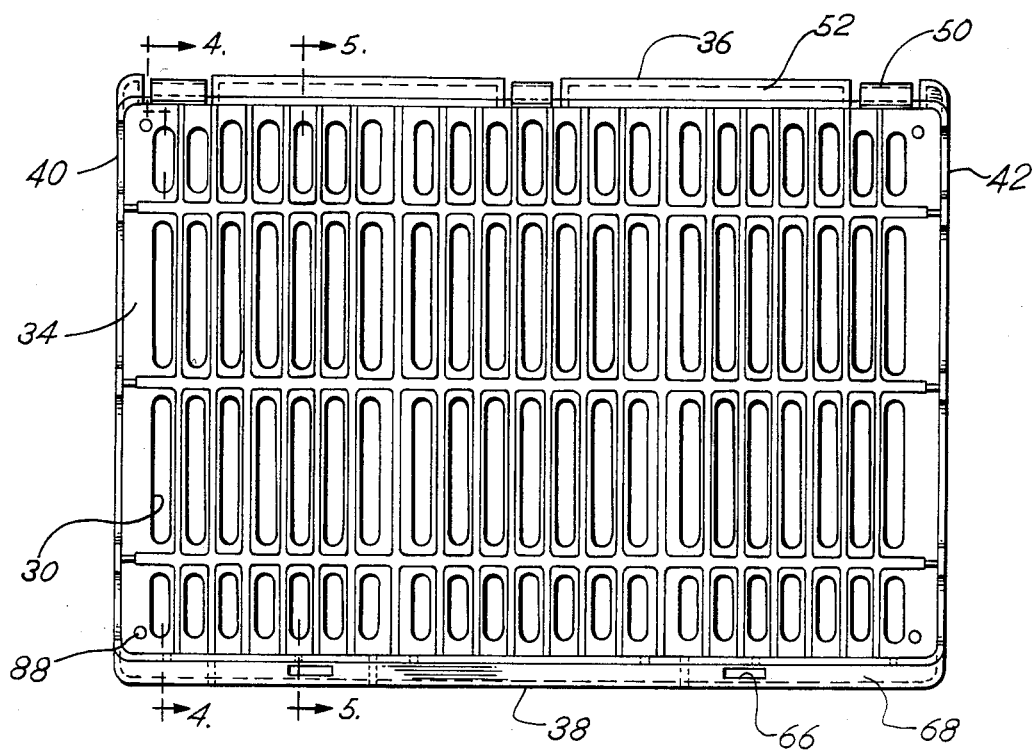
FIG. 3 is a plan view of the casette cover, from the underside.
Figure 4:
FIG. 4 is a first section view of the cover, taken along line 4—4 of FIG. 3.
Figure 5:
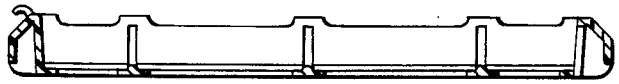
FIG. 5 is a second section view of the cover, taken along line 5—5 of FIG. 3.

A rectangular cover 32 has a top 34 (FIG. 3) and four cover sidewalls 36, 38, 40, 42. The top and cover sidewalls define a cover interior 44 and a cover exterior 46. The top and cover sidewalls are formed of sterilization heat resistant plastic. They are perforated substantially completely with a plurality of the sterilization openings 30 from the cover exterior 46 (FIG. 2) to the cover interior 44.

Hinges 48 (FIG. 2) on the first tray sidewall 18 and the first cover sidewall 36 releasably, hingeably join the first cover sidewall 36 to the first tray sidewall 18 and thereby the cover 32 to the tray 14. The cover 32 and tray 14 are thereby hingedly movable relative to each other about the hinges 48 to and from open and closed positions. The cover 32 and tray 14 are also separable from each other when the top of the cover and the bottom of the tray are substantially perpendicular, or just past true perpendicularity.

The hinges include hinge pins 49 (FIGS. 2,6) on the tray 10, and arcuate hinge flanges 50 (FIGS. 2,3) on the cover 32. The hinge flanges 50 engage and rotate about the hinge pins 49 to and from the closed position and open position. With the cover moved from the closed position just past perpendicularity with the tray, a chamfered or angled first cover sidewall ledge 52 (FIGS. 2,3) along the sidewall 36 rests against a chamfered first tray sidewall ledge 54 (FIG. 6) along the tray sidewall 18. The flanges 50 hold the cover 32 on the tray 14 in this position, unless the cover is lifted upward in a direction generally parallel to the plane of the first tray ledge 54. When the cover is so lifted, the hinge pins 49 disengage from the hinge flanges 50, releasing the cover 32 from the tray 14. The cover 32 is returned to the tray by opposite movement. The hinges 48 thus constitute a form of hinge means on the cover and the tray for releasably hingeably joining the cover to the tray, the cover and tray thereby being separable and being hingedly movable to and from open and closed positions.

As best shown in FIG. 2, the hinge pins 49 and flanges 50 are recessed inward of the common plane defined by the sidewalls 36, 18 when co-planar, in the closed position of the tray and cover. With the recess toward the tray and cover interiors, the common sidewall plane provides a back surface for the stable, upright placement of the casette 10.

The hinges are formed of sterilization heat resistant plastic.

Latches 56 (FIG. 1) are on the second tray sidewall 20 opposite the first tray sidewall 18 and on the second cover sidewall 38 opposite the first cover sidewall 36. The latches 56 releasably latch the second cover sidewall to the second tray sidewall and thereby the cover to the tray in the closed position. The latches are formed of sterilization heat resistant plastic.

Figure 8:
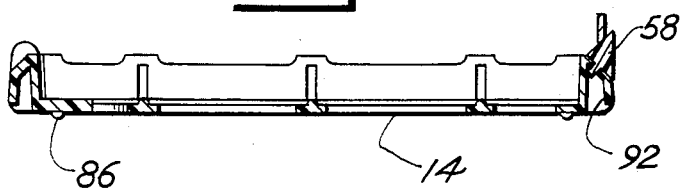
FIG. 8 is a second section view of the casette tray, taken along line 8—8 of FIG. 6.
Figure 9:
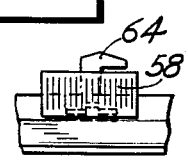
FIG. 9 is a partial, elevation view of the casette tray, showing a latch piece.

The latches 56 include cross-sectionally triangular latch pieces 58 (FIGS. 2,8,9) slidably mounted in slots 60 (FIG. 6) in a second, chamfered, tray ledge 62. The latch pieces 58 include latch keys 64 which operatively cooperate with further slots 66 in a second, chamfered, cover ledge 68. The latch pieces 58 are slidable to and from latching and unlatching positions. In the latching positions, the latch keys 64 extend through the slots 66, and behind portions of the ledge 68 adjacent the slots 66. In the unlatching positions, the latch keys align with the slots 66 and do not extend behind portions of the ledge 68. Thus, the latches 56 constitute one form of a latch means on the cover and tray for releasably latching the cover to the tray in the closed positon.

The latch pieces 58 are recessed inward of the common plane defined by the sidewalls 38, 20 when co-planar, in the closed position of the tray and cover. The common sidewall plane provides a front surface for stable, upright placement of the casette 10.

The sidewalls 22, 40 and 24,42 further provide planar side surfaces for stable, upright placement of the casette.

Instrument compartment rails such as rails 70,72 (FIG. 2) are removably fastened to the cover sidewalls within the cover interior and the tray sidewalls within the tray interior, at corresponding locations. The compartment rails thereby define such instrument compartments as may be preferred within the closed casette. The compartment rails are also formed of sterilization heat resistant plastic.

Instrument locating and retaining rails such as rails 74, 76, 78 (FIG. 2) are removably fastened to the cover sidewalls within the cover interior and the tray sidewalls within the tray interior, and within such instrument compartments as desired. The locating and retaining rails include thereon spaced instrument holders such as nesting recess 80 adapted to snugly, releasably locate and hold instruments in spaced relation to each other away from the tray exterior, away from the cover exterior, and within the instrument compartments. The locating and retaining rails 74, 76 are further formed of sterilization heat resistant plastic.

All the rails are laterally flexible, to be bowed for insertion in the casette 10. Each rail, such as rail 78, has ends with tabs, such as tab 82, of reduced cross section. Each tab is adapted to fit within tabs slots such as slot 84. The tab slots are spaced about all the tray and cover sidewalls, for placement of the rails transversely as shown, or for placement of longer rails longitudinally of the casette. The rails and tab slots thus constitute one form of an instrument retaining means on the cover and tray for reasonably retaining dental instruments within the closed cover and tray remote from contact, in at least a first fixed arrangement in both the open and closed positions of the cover and tray. The rail 78, unlike the other rails, includes a soft, flexible, heat resistant surround silicone over an internal bar. The surround is feathered, or partially, transversely, split in a closely spaced pattern of a plurality of slits, to resiliently press the instruments against the rails 74, 76.

Stacking feet such as foot 86 (FIG. 8) protrude from the tray bottom 16. Stacking feet receptors such as receptor 88 (FIG. 3) are recessed in the cover top 34 corresponding to the stacking feet. The feet and receptors cooperate such that the tray 14 is placeable upon and fixedly supportable atop the cover 32. As desired, the tray of one casette may be stacked atop the cover of another casette, or atop its own cover. A plurality of the casettes may be stacked, or a cover of a single casette simply placed under the casette tray to be out of the way, and save counter space. The feet and receptors thus constitute one form of a stacking means on the cover and tray for stacking the tray over the cover while separated therefrom.

As most preferred, the casette 10, except the silicone of the rail 78, is fully formed of polysulfone. Also as most preferred, the tray 14 and cover 32 are each molded in a single molding step, resulting in complete units of the tray and cover. A single cavity mold with interchangeable inserts for the hinge components is used for both the tray and cover. The latch pieces 58 are forced through the slots 60 when the tray ledge 68 is flexible, during molding of the tray 14. Ribs such as a rib 90 (FIG. 2) crisscross the tray bottom 16 and cover top 34 alongside and between the slots 30 to strengthen the cover 32 and tray 14. All internal and external corners of the casette 10 are rounded, for pleasing appearance and safety of usage. No closed-bottom recess, closed-bottom slot or other closed-bottom opening exists in the casette 10. As an example, a recess 92 (FIG. 8) is formed under the ledge 68. The recess 92 is open, not closed, along the bottom 16 of the tray 14. Contaminant entrapment is thereby avoided. Also, with the recess 92, breakage of a latch piece 58 does not result in entrapment of any broken remnants of the piece 58. The casette 10 can be stacked with other casettes in horizontal or vertical stacks, in any desired orientation of the casettes. The casettes may be loaded with instruments and repeatedly sterilized and used, with the instruments thereby always efficiently arranged. Sterilization may be accomplished by means of autoclave, dry heat, and other suitable sterilization means.

The preferred embodiment is now described. If desired, features of the preferred embodiment may be varied. As an example, the hinge components may be closely toleranced such that the cover, if pivoted in relation to the tray past perpendicularity, will cam off the tray, without needing to be lifted off. To particularly point out and distinctly claim the subject matter regarded as invention, the following claims conclude this specification.

What is claimed is:

1. A sterilizable instrument cassette for repeatedly cycling through a process of use and sterilization, and in which instruments are removably and replaceably kept, comprising:
   a tray formed of sterilization heat resistant plastic perforated with a plurality of sterilization openings;
   a cover formed of sterilization heat resistant plastic perforated with a plurality of sterilization openings;
   means on the tray and cover joining the cover to the tray, the cover and tray thereby being movable relative to each other to and from open and closed positions, the joining means being formed of sterilization heat resistant plastic;
   instrument compartment rails fastened to the cover and the tray at corresponding locations, thereby defining instrument compartments within the cassette, when closed, the compartment rails being formed of sterilization heat resistant plastic; and
   instrument locating and retaining rails fastened within said cassette interior and within the instrument compartments, the locating and retaining rails including thereon spaced instrument holders adapted to releasably hold instruments in spaced relation to each other and the tray and the cover within the instrument compartments, the locating and retaining rails being formed of sterilization heat resistant plastic.

2. A medical/dental instrument casette as in claim 1 in which the tray, cover, latch means, instrument retaining means and stacking means are formed of polysulfone.

3. A medical/dental instrument casette as in claim 1 in which the instrument retaining means is adaptable for releasably retaining dental instruments in a plurality of fixed arrangements.

4. A medical/dental instrument casette as in claim 1 in which the instrument retaining means is removeable from the casette.

5. A medical/dental instrument casette as in claim 1 in which the stacking means comprises protuberances on the tray and corresponding recesses on the cover.

6. An instrument cassette as in claim 1, further comprising:
   latch means releasably latching the cover to the tray in the closed position, the latch means being formed of sterilization heat resistant plastic.

7. A sterilizable, stackable, medical/dental instrument casette for repeatedly cycling through a process of use and sterilization in which instruments are placed and kept in fixed arrangements in casettes, and in which instruments are removed from casettes only for use, repair or replacement of the instruments, the casette being adaptable to a plurality of pre-selected, fixed arrangements of instruments in casettes, comprising:
   a rectangular tray having a bottom and four tray sidewalls defining a tray interior and a tray exterior, the bottom and tray sidewalls being formed of sterilization heat resistant plastic, perforated substantially completely with a plurality of sterilization openings from the tray exterior to the tray interior;
   a rectangular cover having a top and four cover sidewalls defining a cover interior and a cover exterior, the top and cover sidewalls being formed of sterilization heat resistant plastic, perforated substantially completely with a plurality of sterilization openings from the cover exterior to the cover interior;
   hinges on a first tray sidewall and a first cover sidewall releasably, hingeably joining the first cover sidewall to the first tray sidewall and thereby the cover to the tray, the cover and tray thereby being hingedly movable relative to each other about the hinges to and from open and closed positions and being separable from each other when the top of the cover and the bottom of the tray are substantially perpendicular, the hinges being formed of sterilization heat resistant plastic;
   a latch on a second tray sidewall opposite the first tray sidewall and on a second cover sidewall opposite the first cover sidewall, the latch releasably latching the second cover sidewall to the second tray sidewall and thereby the cover to the tray in the closed position, the latch being formed of sterilization heat resistant plastic;
   instrument compartment rails removably fastened to the cover sidewalls within the cover interior and the tray sidewalls within the tray interior, at corresponding locations, the compartment rails thereby defining instrument compartments as preferred within the casette, when closed, the compartment rails being formed of sterilization heat resistant plastic;
   instrument locating and retaining rails removably fastened to the cover sidewalls within the cover interior and the tray sidewalls within the tray interior, and within the instrument compartments, the locating and retaining rails including thereon spaced instrument holders adapted to snugly, releasably locate and hold, as preferred, instruments in spaced relation to each other from the tray exterior and the cover exterior within the instrument compartments, the locating and retaining rails being formed of sterilization heat resistant plastic;
   stacking feet protruding from the tray bottom being formed of sterilization heat resistant plastic; and
   stacking feet receptors recessed in the cover top corresponding to the stacking feet, the receptors being formed of sterilization heat resistant plastic.

8. A medical/dental instrument casette as in claim 7 in which the first cover sidewall and the first tray sidewall are substantially co-planar in the closed position to define a back surface for stable, upright placement of the casette, and in which the hinges are recessed toward the tray interior and the cover interior away from the back surface, in the closed position.

9. A medical/dental instrument casette as in claim 7 in which the second cover sidewall and second tray sidewall are substantially co-planar to define a front surface for stable, upright placement of the casette, and in which the latch is recessed toward the tray interior and the cover interior away from the front surface, in the closed position.

10. A sterilizable, medical/dental instrument cassette for repeatedly cycling through a process of use and sterilization in which instruments are placed and kept in fixed arrangements in cassettes, and in which instruments are removed from cassettes only for use, repair or replacement of the instruments, the cassette being adaptable to pre-selected, fixed arrangements of instruments in cassettes, comprising:

a substantially rectangular tray having a bottom and four tray sidewalls defining a tray interior and a tray exterior, the bottom and tray sidewalls being formed of sterilization heat resistant plastic, perforated with a plurality of sterilization openings from the tray exterior to the tray interior;

a substantially rectangular cover having a top and four cover sidewalls defining a cover interior and a cover exterior, the top and cover sidewalls being formed of sterilization heat resistant plastic, perforated with a plurality of sterilization openings from the cover exterior to the cover interior;

hinges on a first tray sidewall and a first cover sidewall releasably, hingeably joining the first cover sidewall to the first tray sidewall and thereby the cover to the tray, the cover and tray thereby being hingedly movable relative to each other about the hinges to and from open and closed positions and being separable from each other, the hinges being formed of sterilization heat resistant plastic;

at least a latch on a second tray sidewall opposite the first tray sidewall and on a second cover sidewall opposite the first cover sidewall, the latch releasably latching the second cover sidewall to the second tray sidewall and thereby the cover to the tray in the closed position, the latch being formed of sterilization heat resistant plastic;

instrument compartment rails fastened to the cover sidewalls within the cover interior and the tray sidewalls within the tray interior, at corresponding locations, the compartment rails thereby defining instrument compartments as preferred within the cassette, when closed, the compartment rails being formed of sterilization heat resistant plastic; and instrument locating and retaining rails fastened to the cover sidewalls within the cover interior and the tray sidewalls within the tray interior, and within the instrument compartments, the locating and retaining rails including thereon spaced instrument holders adapted to snugly, releasably locate and hold, as preferred, instruments in spaced relation to each other and the tray exterior and the cover exterior within the instrument compartments, the locating and retaining rails being formed of sterilization heat resistant plastic.

11. A sterilizable instrument cassette for repeatedly cycling through a process of use and sterilization, and in which instruments are removably and replaceably kept, comprising:

a tray formed of sterilization heat resistant plastic perforated with a plurality of sterilization openings;

a cover formed of sterilization heat resistant plastic perforated with a plurality of sterilization openings;

means on the tray and cover joining the cover to the tray to define a cassette interior, the cover and tray thereby being movable relative to each other to and from open and closed positions, the joining means being formed of sterilization heat resistant plastic;

instrument compartment rails fastened within said cassette interior, thereby defining instrument compartments within the cassette, the compartment rails being formed of sterilization heat resistant plastic; and instrument locating and retaining rails fastened to the cover and the tray within the instrument compartments, the locating and retaining rails including thereon spaced instrument holders adapted to releasably hold instruments in spaced relation to each other and the tray and the cover within the instrument compartments, the locating and retaining rails being formed of sterilization heat resistant plastic.

* * * * *

UNITED STATES PATENT AND TRADEMARK OFFICE
CERTIFICATE OF CORRECTION

PATENT NO. : 4,541,992

DATED : September 17, 1985

INVENTOR(S) : Charles R. Jerge, Bruce Frankel, Karl Zoll

It is certified that error appears in the above-identified patent and that said Letters Patent is hereby corrected as shown below:

Column 5

In claim 1, lines 25 and 26:

after " fastened", delete "within said cassette interior and" and substitute --to the cover and the tray--.

Column 8
In claim 11, line 22:

after "fastened," delete "to the cover and the tray" and substitute --within said cassette interior and--.

Signed and Sealed this

Twelfth Day of October, 1993

Attest:

BRUCE LEHMAN

Attesting Officer     Commissioner of Patents and Trademarks